(12) United States Patent
Shirono et al.

(10) Patent No.: US 8,465,733 B2
(45) Date of Patent: Jun. 18, 2013

(54) PHARMACEUTICAL COMPOSITION CONTAINING HUMAN MESENCHYMAL STEM CELL

(75) Inventors: Hiroyuki Shirono, Hyogo (JP); Youngjin Byun, Hyogo (JP); Shoichiro Kamei, Hyogo (JP); Kiwamu Imagawa, Hyogo (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 76 days.

(21) Appl. No.: 12/740,758

(22) PCT Filed: Oct. 27, 2008

(86) PCT No.: PCT/JP2008/069404
§ 371 (c)(1),
(2), (4) Date: May 27, 2011

(87) PCT Pub. No.: WO2009/057537
PCT Pub. Date: May 7, 2009

(65) Prior Publication Data
US 2011/0274663 A1    Nov. 10, 2011

(30) Foreign Application Priority Data

Nov. 2, 2007  (JP) ................................. 2007-286778

(51) Int. Cl.
*A01N 63/00* (2006.01)
*C12N 5/00* (2006.01)

(52) U.S. Cl.
USPC .......................................... 424/93.7; 435/325

(58) Field of Classification Search
USPC .......................................... 424/93.7; 435/325
See application file for complete search history.

(56) References Cited

U.S. PATENT DOCUMENTS

| 5,486,359 | A | 1/1996 | Caplan et al. |
| 6,328,960 | B1 | 12/2001 | McIntosh et al. |
| 2011/0262402 | A1* | 10/2011 | Kuroda et al. ............... 424/93.7 |

FOREIGN PATENT DOCUMENTS

| JP | 2004129549 A | 4/2004 |
| JP | 2004201612 A | 7/2004 |
| JP | 2004210713 A | 7/2004 |
| WO | 9222584 A1 | 12/1992 |
| WO | 9623059 A1 | 8/1996 |
| WO | 9903973 A1 | 1/1999 |

OTHER PUBLICATIONS

Luo et al. (A Practical Procedure for the Cryopreservation of Marrow Cells intended for Autotransplantation. Leukemia and Lymphoma, vol. 17, pp. 495-499).*
Ringden, Olle et al. "Mesenchymal Stem Cells for Treatment of Therapy-Resistant Graft-versus-Host Disease." (Transplantation), May 27, 2005, pp. 1390-1397, vol. 81, No. 10.
Bacigalupo, Andrea. "Management of acute graft-versus-host disease." (British Journal of Haematology), 2007, pp. 87-98, No. 137.
Mohyeddin-Bonab, Mandana et al. "Autologous In Vitro Expanded Mesenchymal Stem Cell Therapy for Human Old Myocardial Infarction." (Archives of Iranian Medicine), Oct. 2007, pp. 467-473, vol. 10, No. 4.
JPO Patent Abstracts of Japan: "English language abstract—Selective Growth Method for Mesenchymal Stem Cell From Fat-Derived Cell Group." JP2004129549A, Applicant: Kitagawa Yasuo Apr. 30, 2004.
JPO Patent Abstracts of Japan: "English language abstract—Undifferentiated Multipotential Cell and Method for Preparing Related Tissue or Tooth by Using the Same." JP2004201612A, Applicant: Ueda Minoru Jul. 22, 2004.
JPO Patent Abstracts of Japan: "English language abstract—Medical Cell Preparation Derived From Placenta," JP2004210713A, Applicant: Asahi Kasei Corp Jul. 29, 2004.

* cited by examiner

*Primary Examiner* — Karen Cochrane Carlson
*Assistant Examiner* — Natalie Moss
(74) *Attorney, Agent, or Firm* — Millen, White, Zelano & Branigan, P.C.

(57) ABSTRACT

Disclosed are a method for producing a frozen pharmaceutical composition prepared from cultured human mesenchymal stem cells and a pharmaceutical composition containing human mesenchymal stem cells. This method is a method for producing a frozen pharmaceutical composition containing human mesenchymal stem cells, which comprises the following steps in this order: (a) adding trypsin to human mesenchymal stem cells in a culture vessel to detach the cells from the surface of the culture vessel; (b) adding a bicarbonate Ringer's solution containing human serum albumin to the detached cells to terminate the reaction with trypsin, and washing the cells with the bicarbonate Ringer's solution containing human serum albumin; (c) suspending the cells in a bicarbonate Ringer's solution containing human serum albumin and dimethyl sulfoxide; (d) putting the resulting suspension in a container which allows freezing of what is contained therein, and sealing the container; and (e) freezing the suspension put in the container.

18 Claims, 1 Drawing Sheet

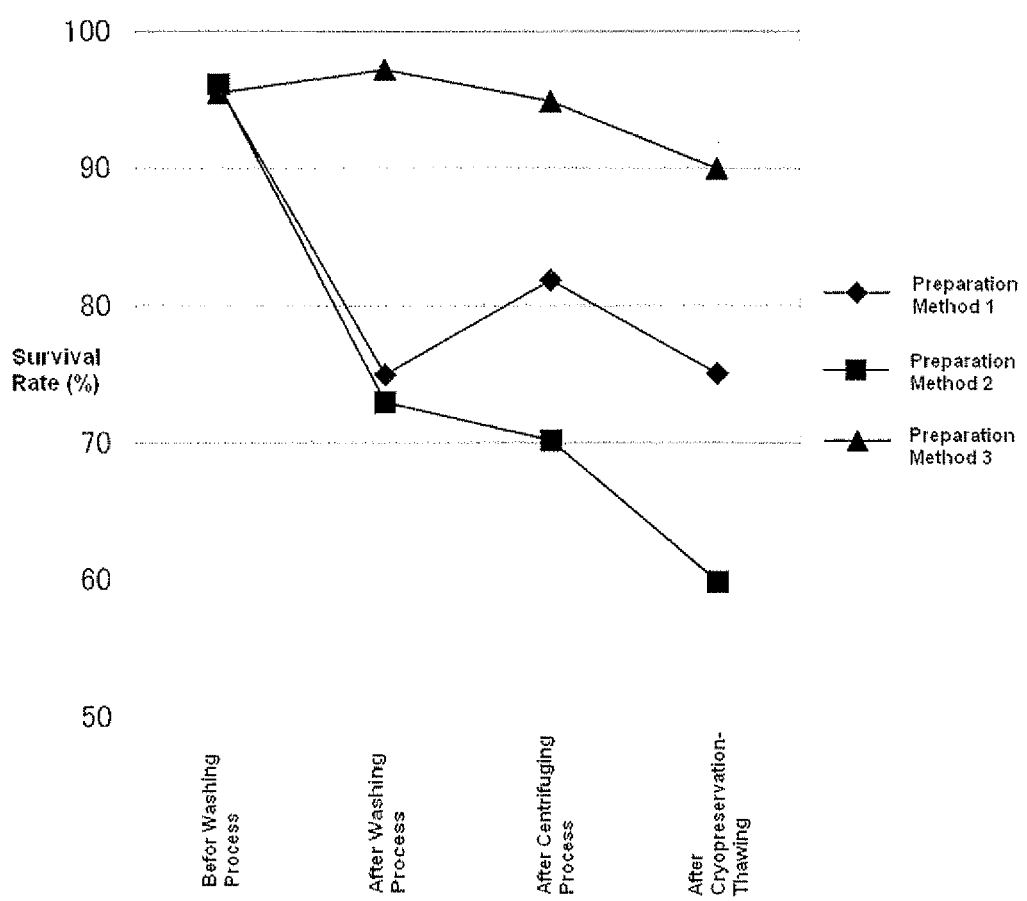

PHARMACEUTICAL COMPOSITION CONTAINING HUMAN MESENCHYMAL STEM CELL

TECHNICAL FIELD

The present invention relates to a frozen pharmaceutical composition containing human mesenchymal stem cells and the method for producing it.

BACKGROUND ART

Mesenchymal stem cells are a multipotent stem cells discovered in bone marrow. Since mesenchymal stem cells have an ability to differentiate into a variety of cell types such as bone cells, cardiac muscle cells, fat cells or the like, it is expected that they can be applied in regenerative medicine in such a manner that they are administered (by injection) to a living body and allowed to transfer to the affected part and differentiate into a tissue needed there (cf. patent document 1 and patent document 2). Also, it has been shown that mesenchymal stem cells can modulate T cell-mediated immune reactions when administered to a living body, and that the cells can be used as a medicine which inhibits rejection after transplantation (cf. patent document 3).

Focusing on the multipotency of and the effect to inhibit rejection by mesenchymal stem cells, clinical studies using human mesenchymal stem cells are going on. For example, led by the U.S. groups, clinical studies are being performed on the therapeutic effect of human mesenchymal stem cells which were collected from a person genetically different from the patients and cultured, on the graft versus host disease (GVHD) occurring after bone marrow transplantation, and their efficacy is being proved (cf. non-patent document 1 and non-patent document 2). Also, a clinical application of human mesenchymal stem cells for myocardium reproduction after occurrence of myocardial infarction is attempted, too (cf. non-patent document 3).

It is known that human mesenchymal stem cells occur in bone marrow fluid. However, their number is very limited. While it is also known that human mesenchymal stem cells are available from various tissues such as adipose tissue (cf. patent document 4), dental pulp tissue (cf. patent document 5), placenta tissue or umbilical cord tissue as well as from bone marrow fluid (cf. patent document 6), the available number of them are very small in any case.

As noted above, human mesenchymal stem cells occurring in the living body are very few. However, a large number of human mesenchymal stem cells can be prepared from a very limited number of human mesenchymal stem cells obtained from bone marrow, through their culture and multiplication using an artificial culture medium (cf. patent document 7). Human mesenchymal stem cells prepared in large numbers in this way can, like other cultured cells, be preserved in a frozen state, and it is known that a frozen culture medium comprising 90% of fetal bovine serum and 10% of dimethyl sulfoxide (DMSO) can be used for cryopreservation (cf. patent document 8). In order for human mesenchymal stem cells to be widely supplied as pharmaceutical products to medical institutions for the treatment of GVHD, myocardium reproduction or the like, it is expected that human mesenchymal stem cells must be transported to the medical institutions in the form of packaged frozen cells to save the cells from possible alteration until the use thereof.

Thus, in order to supply human mesenchymal stem cells in the market as parenteral pharmaceutical products to be administered directly to humans, it is necessary for the products to pass through processes of washing the cells to remove the culture medium used for proliferation thereof and thereafter freezing the cells in a solution which is suitable for the dosage to humans. Generally, each of washing and freezing of the cells, and thawing them before use thereafter gives a major stress to the cells, and some of them are thereby ready to be injured to death. When human mesenchymal stem cells are supplied as pharmaceutical products in a frozen state, it is undesirable, from the viewpoints of maintaining viable cell counts necessary for achieving their pharmaceutical effect, and of their quality control as pharmaceutical products as well, to allow to cause a large number of cell deaths during the processes of preparing frozen cells as pharmaceutical products from cultured cells and of thawing them before use thereafter.

Also, when human mesenchymal stem cells are administered to a patient by intravenous injection, it can be assumed that the cells, after thawed, are added to the infusion fluid in a bag. Therefore, it is desirable that the cells are maintained stable even in the state in which they are, after thawed, added to other infusion fluid and thereby diluted.

[patent document 1] Japanese Patent Application Publication No. H10-512756
[patent document 2] Japanese Patent Application Publication No. 2002-511094
[patent document 3] U.S. Pat. No. 6,328,960
[patent document 4] Japanese Patent Application Publication No. 2004-129549
[patent document 5] Japanese Patent Application Publication No. 2004-201612
[patent document 6] Japanese Patent Application Publication No. 2004-210713
[patent document 7] U.S. Pat. No. 5,486,359
[patent document 8] Japanese Patent Application Publication No. H07-500001
[non-patent document 1] Transplantation. 2006; 81(10): 1390-7
[non-patent document 2] Br J Haematol. 2007; 137(2): 87-98
[non-patent document 3] Arch Iran Med. 2007; 10(4): 467-73

DISCLOSURE OF THE INVENTION

Technical Problem

Against the above mentioned background, the present invention is intended to provide a method for production of a pharmaceutical composition, which method can minimize the number of cell death during the course in which human cultured mesenchymal stem cells are washed, formed into a frozen pharmaceutical composition, and finally thawed when they are used, as well as to provide a pharmaceutical composition containing human mesenchymal stem cells in which composition the number of cell death can be minimized. The present invention is also intended to provide a pharmaceutical composition containing human mesenchymal stem cells that can maintain the cells stable even in a state in which they are, after thawed, added to other infusion fluid and diluted therewith.

Means to Solve the Problem

The inventors of the present invention have found that though human mesenchymal stem cells are very likely to die in a washing process to remove culture medium following their culture for proliferation, their death can be prevented by performing the washing process with a bicarbonate Ringer's solution containing human serum albumin. Furthermore, the inventors have also found that death of human mesenchymal stem cells during their cryopreservation and thawing can remarkably be suppressed by using as the solution in which the cells are to be suspended, a solution prepared by adding dimethyl sulfoxide to a basal bicarbonate Ringer's solution containing human serum albumin. The present invention is based on these findings.

Namely, the present invention provides the following.

1. A pharmaceutical composition which comprises human mesenchymal stem cells in a bicarbonate Ringer's solution containing human serum albumin and dimethyl sulfoxide.

2. A pharmaceutical composition according to 1 above, wherein the bicarbonate Ringer's solution contains as electrolytes bicarbonate ion, sodium ion, potassium ion, calcium ion and chloride ion, and wherein the concentration of sodium ion is 130-145 mEq, the osmotic pressure ratio of the solution to the physiological saline is 0.9-1.1, and the pH of the solution is 6.8-7.8.

3. A pharmaceutical composition according to 1 or 2 above, wherein the bicarbonate Ringer's solution contains 22-28 mEq/L of bicarbonate ion.

4. A pharmaceutical composition according to one of 1 to 3 above, wherein the bicarbonate Ringer's solution further contains magnesium ion and citrate ion as electrolytes.

5. A pharmaceutical composition according to one of 1 to 4 above, wherein the bicarbonate Ringer's solution contains 120-150 mEq/L of sodium ion, 3.6-4.4 mEq/L of potassium ion, 2.7-3.3 mEq/L of calcium ion, 0.9-1.1 mEq/L of magnesium ion, 100-125 mEq/L of chloride ion, 22-28 mEq/L of bicarbonate ion, and 4.5-5.5 mEq/L of citrate ion.

6. A pharmaceutical composition according to one of 1 to 5 above, wherein the concentration of human serum albumin is 0.1-10 W/V %.

7. A pharmaceutical composition according to one of 1 to 5 above, wherein the concentration of human serum albumin is 3-8 W/V %.

8. A pharmaceutical composition according to one of 1 to 7 above, wherein the concentration of dimethyl sulfoxide is 8-12 W/V %.

9. A pharmaceutical composition according to one of 1 to 8 above, wherein the human mesenchymal stem cells are those derived from human bone marrow.

10. A pharmaceutical composition according to one of 1 to 9 above, wherein the composition contains the human mesenchymal stem cells at a density of $1 \times 10^5$-$1 \times 10^8$ cells/mL.

11. A pharmaceutical composition according to one of 1 to 9 above, wherein the composition contains the human mesenchymal stem cells at a density of $1 \times 10^6$-$1 \times 10^7$ cells/mL.

12. A pharmaceutical composition according to one of 1 to 11 above, wherein the composition is held in a sealed container which can allows freezing of what is contained therein.

13. A pharmaceutical composition according to 12 above, wherein the composition is held in the sealed container at a volume of 1-30 mL.

14. A pharmaceutical composition according to one of 1 to 13 above, wherein the composition is in a frozen state.

15. A method for preparation of human mesenchymal stem cells free of the medium used for their culture comprising collecting the human mesenchymal stem cells from a culture vessel in which they were allowed to proliferate, which method further comprises the steps:

(a) adding trypsin to human mesenchymal stem cells in the culture vessel to detach the cells from the surface of the culture vessel, and (b) adding a bicarbonate Ringer's solution containing human serum albumin to the detached human mesenchymal stem cells to terminate the reaction with trypsin while washing the cells with the bicarbonate Ringer's solution containing human serum albumin.

16. A method for preparation according to 15 above, wherein the bicarbonate Ringer's solution contains as electrolytes bicarbonate ion, sodium ion, potassium ion, calcium ion and chloride ion, and wherein the concentration of sodium ion is 130-145 mEq, the osmotic pressure ratio of the solution to the physiological saline is 0.9-1.1, and the pH of the solution is 6.8-7.8.

17. A method for preparation according to 15 or 16 above, wherein the bicarbonate Ringer's solution contains 22-28 mEq/L of bicarbonate ion.

18. A method for preparation according to one of 15 to 17 above, wherein the bicarbonate Ringer's solution further contains magnesium ion and citrate ion as electrolytes.

19. A method for preparation according to one of 15 to 18 above, wherein the bicarbonate Ringer's solution contains 120-150 mEq/L of sodium ion, 3.6-4.4 mEq/L of potassium ion, 2.7-3.3 mEq/L of calcium ion, 0.9-1.1 mEq/L of magnesium ion, 100-125 mEq/L of chloride ion, 22-28 mEq/L of bicarbonate ion, and 4.5-5.5 mEq/L of citrate ion.

20. A method for preparation according to one of 15 to 19 above, wherein the concentration of human serum albumin in the bicarbonate Ringer's solution in step (b) is 0.5-3 W/V %.

21. A method for production of a frozen pharmaceutical composition comprising human mesenchymal stem cells, which method comprises the steps in this order:

(c) suspending the human mesenchymal stem cells prepared by a method of one of 15 to 20 above in a bicarbonate Ringer's solution containing human serum albumin and dimethyl sulfoxide, (d) putting the resulting suspension obtained by step (c) in a container which allows freezing of what is contained therein, and sealing the container, and (e) freezing the suspension put in the container in above (d).

22. A method for production according to above, wherein the concentration of human serum albumin in the bicarbonate Ringer's solution in step (c) is 0.1-10 W/V %.

23. A method for production according to 21 above, wherein the concentration of human serum albumin in the bicarbonate Ringer's solution in step (c) is 3-8 W/V %.

24. A method for production according to one of 21 to 23 above, wherein the concentration of dimethyl sulfoxide in the bicarbonate Ringer's solution in step (c) is 8-12 W/V %.

25. A method for production according to one of 21 to 24 above, wherein the human mesenchymal stem cells are suspended at a density of $1 \times 10^5$-$1 \times 10^6$ cells/mL in step (c).

26. A method for production according to one of 15 to 24 above, wherein the human mesenchymal stem cells are suspended at a density of $1 \times 10^6$-$1 \times 10^7$ cells/mL in step (c).

Effect of the Invention

The pharmaceutical composition of the present invention effectively prevents death of human mesenchymal stem cells during cryopreservation and thawing thereof, and thus achieves a high cell survival rate. Consequently, according to the pharmaceutical composition of the present invention, decrease in viable cell counts is blocked to be minimal between the human mesenchymal stem cells in the cell suspension to be subjected to the process of freezing and the human mesenchymal stem cells contained in the pharmaceutical composition of the present invention immediately after thawed for use following a period of cryopreservation, thus allowing very easy maintenance and control of the quality as a pharmaceutical product. Also, the pharmaceutical composition of the present invention can maintain a high cell survival rate even in a state in which they are, after thawed, diluted with an infusion fluid. Consequently, the pharmaceutical composition of the present invention, after thawed, can be added to other infusion fluid in a drip bag, diluted, and administered to a patient together with the infusion fluid. It is therefore highly useful.

Also, according to the method of the present invention for preparation of human mesenchymal stem cells using a bicarbonate Ringer's solution containing human serum albumin, death of human mesenchymal stem cells is surely prevented which death otherwise is brought about while washing them after culture (removing the culture medium). This is in contrast with the extremely high death rate (a low survival rate) of human mesenchymal stem cells observed using other solutions than bicarbonate Ringer's solution, giving an outstanding advantage to the method of the present invention. Further, the method of the present invention for production of a frozen pharmaceutical composition containing human mesenchymal stem cells, which method includes in itself the above-mentioned methods for preparation, has advantages that it allows to prepare a pharmaceutical composition suitable to be administered to humans avoiding decrease by death in the number of cultured human mesenchymal stem cells, and that it also allows to provide a pharmaceutical composition in which the decrease in viable cell counts after it is thawed is prevented to be minimal. Thus, this method for production allows stable production of a frozen pharmaceutical composition containing human mesenchymal stem cells in uniform quality.

BRIEF DESCRIPTION OF DRAWINGS

FIG. 1 is a graph showing changes in survival rate of human mesenchymal stem cells in each preparation method.

BEST MODE FOR CARRYING OUT THE INVENTION

Human mesenchymal stem cells, even if they are administered by injection to a patient genetically different from the person from whom it is derived, do not elicit immune reactions such as rejection. On the contrary, they, gathering by themselves at tissues where inflammation is taking place or other injured tissues of the patient, exhibit outstanding therapeutic effects, for example, suppression of increased immune reactions, or repairment of defective tissues by proliferating and differentiating there. Human mesenchymal stem cells can be administered to a patient for treatment even if they are derived from a person different from the patient. Therefore the pharmaceutical composition of the present invention can be produced and cryopreserved beforehand using human mesenchymal stem cells which were collected from a individual and cultured to proliferate, in order to be administered, after it is thawed at a medical institution, to a patient for treatment who is a different person from the donor from whom the mesenchymal stem cells were derived.

The pharmaceutical composition of the present invention comprises human mesenchymal stem cells in a bicarbonate Ringer's solution containing human serum albumin and dimethyl sulfoxide. The pharmaceutical composition of the present invention will usually be supplied to the medical market in a frozen state in order to secure stability of the composition during possible long term storage at medical institutions.

In the present invention, the bicarbonate Ringer's solution is an infusion fluid which is an electrolyte solution (a Ringer's solution) of a type containing bicarbonate ion. In the present invention, the human mesenchymal stem cells are provided in a state where they are suspended in a bicarbonate ion containing albumin and dimethyl sulfoxide (DMSO) (usually in a frozen form), and are preserved in a frozen state, for example, using liquid nitrogen (e.g., approximately $-130°$ C.), until when they are used. In such a frozen state, the human mesenchymal stem cells can, like other cells in general, be maintained semipermanently in the pharmaceutical composition of the present invention.

In the present invention, a preferable bicarbonate Ringer's solution contains as electrolytes bicarbonate ion, sodium ion, potassium ion, calcium ion and chloride ion, and the concentration of sodium ion is 130-145 mEq, the osmotic pressure ratio of the solution to the physiological saline is 0.9-1.1. It is preferable that pH of the bicarbonate Ringer's solution is 6.8-7.8. Also, though the concentration of bicarbonate ion is most preferably 22-28 mEq/L, it is not necessarily limited thereto, and a concentration which is somewhat higher or lower than the range may be used.

In the above, a bicarbonate Ringer's solution may contain magnesium ion and/or citrate ion. A particularly preferred example as a bicarbonate Ringer's solution is the following Composition PP.

| <Composition PP> | |
|---|---|
| Sodium ion: | 120-150 mEq/L |
| Potassium ion: | 3.6-4.4 mEq/L |
| Calcium ion: | 2.7-3.3 mEq/L |
| Magnesium ion: | 0.9-1.1 mEq/L |
| Chloride ion: | 100-125 mEq/L, |
| Bicarbonate ion: | 22-28 mEq/L |
| Citrate ion: | 4.5-5.5 mEq/L |

Also, one embodiment of such a bicarbonate Ringer's solution is the following composition E.

| <Composition E> | |
|---|---|
| Sodium ion: | 135 mEq/L |
| Potassium ion: | 4 mEq/L |
| Calcium ion: | 3 mEq/L |
| Magnesium ion: | 1 inEq/L |
| Chloride ion: | 113 mEq/L, |
| Bicarbonate ion: | 25 mEq/L |
| Citrate ion: | 5 mEq/L |

In the pharmaceutical composition of the present invention, the concentration of human serum albumin is preferably 0.1-10 W/V %, and more preferably 3-8 W/V %. A preferred example of the concentration is 5 W/V %. The human serum albumin may be, but is not limited to, one which is prepared from human serum, and a recombinant human serum albumin may also be used.

In the pharmaceutical composition of the present invention, the concentration of dimethyl sulfoxide is preferably 8-12 W/V %, and a preferred example thereof is 10 W/V %.

Human mesenchymal stem cells obtained from any tissue, such as bone marrow, adipose tissue, dental pulp tissue, placenta tissue, umbilical cord tissue, may be used for the pharmaceutical composition of the present invention. Of the above cells, those derived from bone marrow are preferable e.g., from the viewpoint of its easy availability. Also, it is preferable that the density of viable human mesenchymal stem cells is $1\times10^5$-$1\times10^8$ cells/mL, and more preferably $1\times10^6$-$1\times10^7$ cells/mL. A preferred example of the density is $7.7\times10^6$ cells/mL.

The pharmaceutical composition of the above mentioned invention may be put in a hermetic container, and then frozen. There is no particular limitation as to a hermetic container used for this, and it may be in any appropriate form as far as it can hermetically contain the cells and allows their cryopreservation. For example, one may use a container made of similar materials and in a similar form to those of infusion bags which are widely used in the medical field. The volume of the pharmaceutical composition put in a container is set as desired depending upon therapeutic purpose, however, it may be, for example, 1-30 mL, considering the situation that the pharmaceutical composition of the present invention can be widely used for various kinds of diseases with different levels of severity, and further, for example, 10-20 mL, or 15 mL or the like, considering an extra cost brought about by having too many product lines. The pharmaceutical composition of the present invention which was put in a sealed container in this way and supplied to medical institutions in a frozen state is thawed in the medical institutions, and then administered to a patient parenterally (e.g., by injection or intravenous drip). As for an administration route thereof, injection can be done such as intravenous, intramuscular, subcutaneous, submucous, intraperitoneal or intraocular injection, and injection in any other appropriate parts. The pharmaceutical composition of the present invention may be administered to a patient directly or together with other infusion fluid in a drip bag to which fluid it is added and diluted therewith.

A method for production of the pharmaceutical composition of the present invention is carried out by collecting human mesenchymal stem cells from a culture vessel in which they were allowed to proliferate, preparing the cells so that they are free of the culture medium used for their culture, suspending them in a bicarbonate Ringer's solution containing human serum albumin and dimethyl sulfoxide, putting the suspension in a container, sealing the container, and freezing the suspension.

Human mesenchymal stem cells allowed to proliferate in a culture vessel adhere to the surface of the culture vessel, and trypsin is added to the human mesenchymal stem cells in the culture vessel in order to detach them from the surface of the vessel. The method to detach the cells from the wall of a culture vessel by addition of trypsin is well-known, and those skilled in the art can set the quantity of trypsin to be added appropriately. For example, 0.05% trypsin-EDTA solution can be used. Subsequently, a bicarbonate Ringer's solution containing human serum albumin is added to the human mesenchymal stem cells, which were detached from the surface of the vessel by addition of trypsin, to thereby terminate the reaction with trypsin, and the cells then are washed by a bicarbonate Ringer's solution including human serum albumin. This washing process is a step to remove contaminants such as the culture medium or trypsin contained in the suspension of the human mesenchymal stem cells which were allowed to proliferate by culture. The washing process may be conducted following any appropriate procedure using any appropriate apparatus as far as the above contaminants are substantially removed. For example, but without limitation, it may be conducted using a commercially available closed system automatic cell washing apparatus and/or by centrifugation. Also washing efficiency [(concentration of contaminants after a washing process/concentration of contaminants before the washing process) times] in the washing process can, if desired, be adjusted to 100-1,000,000 times. Through this washing process, the contaminants such as the culture medium used for proliferation of the cells, added trypsin, etc. are substantially removed, and thus, human mesenchymal stem cells free of such contaminants are prepared. In this washing process, the use of the bicarbonate Ringer's solution containing human serum albumin is indispensable in order to prevent decrease in viable cell counts. The concentration of human serum albumin herein may be in the range of 0.1-10 W/V %. The concentration may be either lower than or the same as that of albumin in the bicarbonate Ringer's solution containing albumin and dimethyl sulfoxide which solution is used in the freezing step described hereinafter. Even in the latter case, there is no particular problem except an extra cost thereby brought about. More preferably, the concentration of human serum albumin in this washing step is 0.5-3 W/V %, more preferably 0.5-2 W/V %. A preferred example of the concentration is 1.2 W/V %. It is to be noted that human serum albumin employed here may be, but is not limited to, one which is prepared from human serum, and recombinant human serum albumin may also be employed.

In producing a frozen pharmaceutical composition of the present invention by freezing the above-prepared human mesenchymal stem cells free of the culture medium used for the proliferation of the cells (and trypsin added later), the cells are suspended in a bicarbonate Ringer's solution containing human serum albumin and dimethyl sulfoxide (DMSO). The concentration of human serum albumin in bicarbonate Ringer's solution used in this process may be 0.1-10 W/V %, and it is more preferably 3-8 W/V %. A preferred example of the concentration is 5 W/V %. Also, a preferred concentration of dimethyl sulfoxide in this process is 8-12 W/V %, and a preferred example of the concentration is 10 W/V %.

Freezing of the suspension containing human mesenchymal stem cells obtained above can be performed in a manner generally conducted in cryopreservation of cells. For example, a procedure can be followed in which the suspension is cooled to −6° C. by one ° C. per minute, then refrigerated quickly, and cryopreserved at −130° C. Liquid nitrogen may be used for cryopreservation.

EXAMPLES

The present invention is described in further detail below with reference to examples. However, it is not intended that the present invention be limited to the examples.

[Culture of Human Mesenchymal Stem Cells]

Cryopreserved human mesenchymal stem cells (approximately $2\times10^8$ cells each) were thawed in a thermostatic bath at 37° C., and suspended in 1.5 L of a culture medium [DMEM medium containing 4 mmol/L of L-alanyl-L-glutamine and 10% of FBS (HyClone Laboratories, Inc.)] that had been warmed to 37° C. beforehand, and the suspension was put in a culture vessel (area for culture, 6,300 cm$^2$). Culture was performed in the presence of 5% $CO_2$ at 37° C. until the cells became confluent while changing the culture medium for every 3-4 days.

[Washing of Human Mesenchymal Stem Cells]

The culture medium was removed from the culture vessel, and 400 mL of 0.05% trypsin-EDTA solution (Invitrogen Company) was brought into contact with the cells, and the mixture was left to stand at 37° C. for 15 minutes to detach the cells from the culture vessel. The enzyme reaction was terminated by adding 100 mL of a cell washing solution [an acetate Ringer's solution (PlasmaLyteA, Baxter Corporation) containing 1.2% of human serum albumin (Kenketsu albumin-Nichiyaku, Nihon Pharmaceutical)], and the mixture was divided into portions each containing approximately $5\times10^7$ cells. Part of the cells after this division were sampled and used for measurement of the survival rate (Before Washing Process). The divided set of cell suspensions (each containing approximately $5\times10^7$ cells) were washed following the procedure described below using the washing solutions shown as Preparation Methods 1-3 on Table 1, respectively.

The cell suspension was divided, and placed in a closed system automatic cell washing apparatus (CytoMate Cell Processing System, 4R9860, Baxter Inc.), and washed with the washing solutions shown in Table 1, respectively, setting washing efficiency at 300 times. Part of the cells after washing were sampled and used for measurement of the survival rate (After Washing Process). In Preparation Methods 1 and 2, acetate Ringer's solutions [PlasmaLyteA (Baxter Inc.) and Physio 140 (Otsuka Pharmaceutical), respectively] were employed as washing solutions, and Preparation Method 3, bicarbonate Ringer's solution [Bicarbon-Chu (Ajinomoto Co., Inc.)], to each of which 1.2 W/V % of human serum albumin had been added. The composition of each washing solutions is shown in Table 2, and their electrolyte concentration in Table 3, respectively.

TABLE 1

Composition of Cell Washing Solutions and Cryopreservation Fluids

| | Composition of Washing solutions | Composition of Cryopreservation Fluids |
|---|---|---|
| Preparation Method 1 | PlasmaLyteA containing 1.2% of human serum albumin | PlasmaLyteA containing 20% of DMSO and 8.8% of human serum albumin |
| Preparation Method 2 | Physio 140 containing 1.2% of human serum albumin | Physio 140 containing 20% of DMSO and 8.8% of human serum albumin |
| Preparation Method 3 | Bicarbon-Chu containing 1.2% of human serum albumin | Bicarbon-Chu containing 20% of DMSO and 8.8% of human serum albumin |

TABLE 2

Composition of Each Ringer's Solution

| Type | PlasmaLyteA Acetate Ringer's Solution | | Pysio 140 Acetate Ringer's Solution | | Bicarbon-Chu Bicarbonate Ringer's Solution | |
|---|---|---|---|---|---|---|
| Composition/ 1000 ml | Sodium Chloride | 5.26 g | Sodium Chloride | 6.37 g | Sodium Chloride | 6.14 g |
| | Sodium Gluconate | 5.02 g | Potassium Chloride | 0.298 g | Potassium Chloride | 0.30 g |
| | Sodium Acetate trihydrate | 3.68 g | Calcium Gluconate | 0.673 g | Calcium Chloride dihydrate | 0.22 g |
| | Potassium Chloride | 0.37 g | Magnesium Chloride | 0.203 g | Magnesium Chloride hexahydrate | 0.10 g |
| | Magnesium Chloride hexahydrate | 0.3 g | Anhydrous Sodium Acetate | 2.051 g | Sodiumu Bicarbonate | 2.1 g |
| | | | Sodium Citrate | 0.588 g | Sodium Citrate dihydrate | 0.49 g |
| | | | Glucose | 10 g | | |
| PH | 6.5~8.0 | | 5.9~6.2 | | 6.8~7.8 | |

TABLE 3

Electrolyte Concetration of Each Ringer's Solution

| | | PlasmaLyteA | Physio 140 | Bicarbon-Chu |
|---|---|---|---|---|
| Electro-lyte (mEq/L) | $Na^+$ | 140 | 140 | 135 |
| | $K^+$ | 5 | 4 | 4 |
| | $Ca^{2+}$ | — | 3 | 3 |
| | $Mg^{2+}$ | 3 | 2 | 1 |
| | $Cl^-$ | 98 | 115 | 113 |
| | Acetate ion | 27 | 25 | — |
| | Bicarbonate ion | — | — | 25 |
| | Gluconate ion | 23 | 3 | — |
| | Citrate ion | — | 6 | 5 |

[Centrifugation]

After the washing of the cells with the closed system automatic cell washing apparatus in the process of the "Washing of human mesenchymal stem cells" above was completed, each cell suspension was centrifuged (1500 rpm, ten minutes), and the supernatant thereof was removed. The cells were suspended in a washing solution, and centrifuged (1500 rpm, ten minutes) again, and the supernatant thereof was removed. Part of cells after centrifugation was sampled, and used for measurement of the survival rate (After Centrifuging Process).

[Cryopreservation of Human Mesenchymal Stem Cells]

Cells were suspended in each washing solutions and to which an equal amount of cryopreservation fluids [Ringer's solutions containing 20% DMSO (Edwards Lifescience Research Medical Inc.), and 8.8% of human serum albumin (Nihon Pharmaceutical)] as shown in Table 1 were further added and mixed so that densities of viable cells became $1.53\times10^7$ cells/mL, and each mixture was dispensed into tubes of one mL. The final composition of each cryopreservation fluid containing human mesenchymal stem cells which was prepared according to Preparation Methods 1-3 is shown in Table 4, respectively.

TABLE 4

Final Composition of Each Cryopreservation Fluid Containing Human Mesenchymal Stem Cells

| | Final Composition of Each Cryopreservation Fluid Containing Human Mesenchymal Stem Cells |
|---|---|
| Preparation Method 1 | PlasmaLyteA containing $1.53\times10^7$ Cells/mL of human mesenchymal stem cells, 10% of DMSO and 5% of human serum albumin |
| Preparation Method 2 | Physio 140 containing $1.53\times10^7$ Cells/mL of human mesenchymal stem cells, 10% of DMSO and 5% of human serum albumin |
| Preparation Method 3 | Bicarbon-Chu containing $1.53\times10^7$ Cells/mL of human mesenchymal stem cells, 10% of DMSO and 5% of human serum albumin |

Each cryopreservation fluid containing human mesenchymal stem cells prepared according to Preparation Methods 1 to 3 above and dispensed into the tubes was cooled to −6° C. at the rate of one ° C. per one minute, then refrigerated quickly, and cryopreserved at −130° C.

The human mesenchymal stem cells (approximately 2×10⁸ cells each) cryopreserved in the above were thawed in a thermostatic bath at 37° C., and then, diluted with the culture medium 10 times in volume which had been warmed to 37° C. beforehand. Part of them was used for measurement of the survival rate (After Cryopreservation-Thawing).

[Measurement of Survival Rate of Humans Mesenchymal Stem Cells]

Survival rates of the cells sampled as described above in the steps of Before Washing Process, After Washing Process, After Centrifuging Process and After Cryopreservation-Thawing were measured using a cell function analysis apparatus (Guava EasyCyte, GE Healthcare Biosciences Company). "Survival rate" herein is a value to be shown as ratio (%) of viable cells to whole sampled cells.

The survival rate of cells of each sample is shown in FIG. 1. The cell survival rate in Before Washing Process (i.e., immediately after the cells were detached and collected from the culture vessel) was approximately 96% by any of Preparation Methods 1 to 3.

In Preparation Methods 1 and 2, cell survival rates in After Washing Process were 75% and 73%, respectively, decreasing by more than 20% in comparison with those in Before Washing Process. On the other hand, cell survival rate in After Washing Process in Preparation Method 3 was 97.2%, being maintained at the level of survival observed before washing. Thus, it was found that the decrease in cell survival rate can be prevented according to Preparation Method 3 in the washing process with the closed system automatic cell washing apparatus. The result shows that it is very effective to use the bicarbonate Ringer's solution as a washing solution in the cell washing process in order to prevent decrease in cell survival rate of human mesenchymal stem cells in the washing process.

In Preparation Methods 2 and 3, the cell survival rates in After Centrifuging Process were 70.2% and 94.9%, respectively, decreasing by 2 to 3% in comparison with those in After Washing Process. On the other hand, the cell survival rate in After Centrifuging Process Preparation Method 1 was 81.9%, increasing in comparison with those in After Washing Process (75%). This was an apparent increase in survival rate which resulted from the fact that many dead cells did not precipitate by centrifugation but still remained in the supernatant, and as a result, had been removed together with the supernatant (data not shown). In Preparation Method 2 also, many dead cells did not precipitate by centrifugation but removed together with the supernatant like in Preparation Method 1 (data not shown), yet, as a considerable number of dead cells were still present in the precipitated cells, the survival rate decreased to 70.2%. In contrast with these, the cell death in the centrifugation process was actually prevented in Preparation Method 3, and as a result, the survival rate was maintained at 94.9%.

In Preparation Methods 1 and 2, the cell survival rates of After Cryopreservation-Thawing were 75.1% and 59.9%, respectively. On the other hand, in Preparation Method 3, the cell survival rate was maintained at an extremely high value of 90%. This result shows that the cell survival rate can be maintained at a high value by using a cryopreservation fluid containing the bicarbonate Ringer's solution on refrigerating human mesenchymal stem cells.

[Recovery Rate of Human Mesenchymal Stem Cells]

Recovery rates of viable mesenchymal stem cells obtained by Preparation Methods 1 to 3 described in above examples were measured after culturing the human mesenchymal stem cells in a scaled up manner. Each recovery rate of viable cells was determined by measuring viable cell counts in After Washing Process, After Centrifuging Process and After Cryopreservation-Thawing, respectively, under the condition that the viable cell count in Before Washing Process was adjusted at approximately 2.5×10⁹ cells.

As a result, Preparation Method 3, the recovery rates of viable cells in After Washing Process, After centrifuging Process and After Cryopreservation-Thawing were found to be a high value, i.e., 78.9%, 80.4% and 74.8%, respectively, in comparison with those in Before Washing Process (Table 5). On the other hand, the recovery rates of viable cells in After Washing Process, After centrifuging Process and After Cryopreservation-Thawing Preparation Method 1 were 64.9%, 58.1% and 51.2%, respectively, and that Preparation Method 2 were 59.9%, 58.0% and 52.3%, respectively (Table 5). Namely, the recovery rates Preparation Methods 1 and 2 showed lower values than those Preparation Method 3. This result shows that human mesenchymal stem cells can efficiently be recovered as viable cells according to Preparation Method 3.

TABLE 5

Recovery Rates of Human Mesenchymal stem cells

| | Preparation Method 1 | Preparation Method 2 | Preparation Method 3 |
|---|---|---|---|
| Viable Cell Count of Before Washing Process (×10⁹ Cells) | 2.48 | 2.62 | 2.46 |
| Viable Cell Count of After Washing Process (×10⁹ Cells) | 1.61 | 1.57 | 1.94 |
| Recovery Rate of Viable Cell of After Washing Process (%) | 64.9 | 59.9 | 78.9 |
| Viable Cell Count of After Centrifuging Process (×10⁹ Cells) | 1.44 | 1.52 | 1.98 |
| Recovery Rate of Viable Cell of After Centrifuging Process (%) | 58.0 | 58.0 | 80.4 |
| Viable Cell Count of After Cryopreservation-Thawing (×10⁹ Cells) | 1.27 | 1.37 | 1.84 |
| Recovery Rate of Viable Cell of After Cryopreservation-Thawing (%) | 51.2 | 52.3 | 74.8 |

[Stability of Cells after Cryopreservation-Thawing]

It may happen that cryopreserved human mesenchymal stem cells, after thawed and then added to other infusion fluid in a drip bag and diluted therewith, be administered to a patient together with the infusion fluid. In this regard, cryopreserved cells were thawed, diluted to 2.67 times with an infusion fluid, and left to stand at room temperature. The survival rates of the cells 3, 6, and 24 hours after their dilution were measured relative to viable cell counts immediately after the dilution which counts were regarded as 100%. The measurement was carried out only for the cells prepared by Preparation Methods 1 and 3. As the dilution fluid, Plasma-LyteA was used for the cells prepared by Preparation Method 1, and Bicarbon for the cells prepared by Preparation Method 3.

When the survival rates until six hours after dilution were compared, though the cells prepared by Preparation Method 3 showed the survival rate that was slightly higher than the cells prepared by Preparation Method 1, both of them were kept at a high value of not less than 85% and the difference between them was not significant (Table 6). However, when compared at 24 hours after dilution, the survival rate Preparation Method 3 was kept at 55.8%, i.e., more than half of the cells remained viable. On the other hand, that in Preparation Method 1 was only 26.7% (Table 6). The result shows that regarding the cells prepared by Preparation Method 3, the stability in After Cryopreservation-Thawing is still high even in the state in which the cells are added to other infusion fluid in a drip bag, diluted therewith, and stored for many hours.

TABLE 6

Recovery Rates of Cell of After Cryopreservation-Thawing (%)

| | Just after the Dilution | 3 Hours after the Dilution | 6 Hours after the Dilution | 24 Hours after the Dilution |
|---|---|---|---|---|
| Preparation Method 1 | 100 | 86.8 | 85.8 | 26.7 |
| Preparation Method 3 | 100 | 89.5 | 87.2 | 55.8 |

| | |
|---|---|
| Human mesenchymal stem cells: | $7.65 \times 10^6$ cells |
| Human serum albumin: | 5% |
| Dimethyl sulfoxide: | 10% |
| Bicarbonate Ringer's solution: | to 15 mL |

Human mesenchymal stem cells are suspended, and then added to and sealed in a dialysis bag, cryopreserved, and transported to medical institutions in a frozen state. When used, they are thawed and administered to a patient.

Industrial Applicability

The pharmaceutical composition of the present invention effectively prevents death of human mesenchymal stem cells during cryopreservation and thawing thereof, achieving a high cell survival rate. Thus, according to the pharmaceutical composition of the present invention, maintenance of the quality as pharmaceutical products containing human mesenchymal stem cells becomes very easy. Also, the pharmaceutical composition of the present invention can maintain a high cell survival rate even in the state in which they, after thawed, are diluted with an infusion fluid. Consequently, the pharmaceutical composition of the present invention can, after it is thawed and then added to other infusion liquid in a drip bag and diluted therewith, be administered to a patient together with the infusion fluid, and is therefore highly useful. Also, since the method of the present invention for preparation of human mesenchymal stem cells can surely prevents cell death which otherwise is brought about while their washing, it is useful in production of a pharmaceutical composition containing human mesenchymal stem cells. Further, the method of the present invention for production of a pharmaceutical composition, which method includes in itself the method for preparation, is advantageous in that it allows to produce a frozen pharmaceutical composition containing human mesenchymal stem cells with a stable quality.

We claim:

1. A pharmaceutical composition which comprises human mesenchymal stem cells in a bicarbonate Ringer's solution containing human serum albumin, dimethyl sulfoxide, 120-150 mEq/L of sodium ion, 3.6-4.4 mEq/L of potassium ion, 2.7-3.3 mEq/L of calcium ion, 0.9-1.1 mEq/L of magnesium ion, 100-125 mEq/L of chloride ion, 22-28 mEq/L of bicarbonate ion, and 4.5-5.5 mEq/L of citrate ion.

2. The pharmaceutical composition according to claim 1, wherein the osmotic pressure ratio of the solution to the physiological saline is 0.9-1.1, and the pH of the solution is 6.8-7.8.

3. The pharmaceutical composition according to claim 1, wherein the concentration of human serum albumin is 3-8 W/V %.

4. The pharmaceutical composition according to claim 1, wherein the concentration of dimethyl sulfoxide is 8-12 W/V %.

5. The pharmaceutical composition according to claim 1, wherein the human mesenchymal stem cells are those derived from human bone marrow.

6. The pharmaceutical composition according to claim 1, wherein the composition contains the human mesenchymal stem cells at a density of $1 \times 10^5$-$1 \times 10^8$ cells/mL.

7. The pharmaceutical composition according to claim 1, wherein the composition contains the human mesenchymal stem cells at a density of $1 \times 10^6$-$1 \times 10^7$ cells/mL.

8. The pharmaceutical composition according to claim 1, wherein the composition is held in a sealed container which can allow freezing of what is contained therein.

9. The pharmaceutical composition according to claim 8, wherein the composition is held in the sealed container at a volume of 1-30 mL.

10. The pharmaceutical composition according to claim 1, wherein the composition is in a frozen state.

11. A method for preparation of human mesenchymal stem cells free of the medium used for their culture comprising collecting the human mesenchymal stem cells from a culture vessel in which they were allowed to proliferate, which method further comprises the steps:
   (a) adding trypsin to human mesenchymal stem cells in the culture vessel to detach the cells from the surface of the culture vessel, and
   (b) adding a bicarbonate Ringer's solution containing human serum albumin to the detached human mesenchymal stem cells to terminate the reaction with trypsin while washing the cells with the bicarbonate Ringer's solution containing human serum albumin, 120-150 mEq/L of sodium ion, 3.6-4.4 mEq/L of potassium ion, 2.7-3.3 mEq/L of calcium ion, 0.9-1.1 mEq/L of magnesium ion, 100-125 mEq/L of chloride ion, 22-28 mEq/L of bicarbonate ion, and 4.5-5.5 mEq/L of citrate ion.

12. The method for preparation according to claim 11, wherein the, the osmotic pressure ratio of the solution to the physiological saline is 0.9-1.1, and the pH of the solution is 6.8-7.8.

13. The method for preparation according to claim 11, wherein the concentration of human serum albumin in the bicarbonate Ringer's solution in step (b) is 0.5-3 W/V %.

14. A method for production of a frozen pharmaceutical composition comprising human mesenchymal stem cells, which method comprises the steps in this order:
   (c) suspending the human mesenchymal stem cells prepared by a method of claim 11 above in a bicarbonate Ringer's solution containing human serum albumin, dimethyl sulfoxide, 120-150 mEq/L of sodium ion, 3.6-4.4 mEq/L of potassium ion, 2.7-3.3 mEq/L of calcium ion, 0.9-1.1 mEq/L of magnesium ion, 100-125 mEq/L of chloride ion, 22-28 mEq/L of bicarbonate ion, and 4.5-5.5 mEq/L of citrate ion,
   (d) putting the resulting suspension obtained by step (c) in a container which allows freezing of what is contained therein, and sealing the container, and
   (e) freezing the suspension put in the container in above (d).

15. The method for production according to claim 14, wherein the concentration of human serum albumin in the bicarbonate Ringer's solution in step (c) is 3-8 W/V %.

16. The method for production according to claim 14, wherein the concentration of dimethyl sulfoxide in the bicarbonate Ringer's solution in step (c) is 8-12 W/V %.

17. The method for production according to claim 14, wherein the human mesenchymal stem cells are suspended at a density of $1\times10^5$-$1\times10^8$ cells/mL in step (c).

18. The method for production according to claim 14, wherein the human mesenchymal stem cells are suspended at a density of $1\times10^6$-$1\times10^7$ cells/mL in step (c).

\* \* \* \* \*

UNITED STATES PATENT AND TRADEMARK OFFICE
CERTIFICATE OF CORRECTION

PATENT NO. : 8,465,733 B2
APPLICATION NO. : 12/740758
DATED : June 18, 2013
INVENTOR(S) : Hiroyuki Shirono et al.

It is certified that error appears in the above-identified patent and that said Letters Patent is hereby corrected as shown below:

In the Claims

Column 14, line 43, reads "wherein the, the", should read --wherein the--.

Signed and Sealed this
Seventeenth Day of September, 2013

Teresa Stanek Rea
*Deputy Director of the United States Patent and Trademark Office*